(12) United States Patent
Baylis et al.

(10) Patent No.: US 7,337,685 B2
(45) Date of Patent: Mar. 4, 2008

(54) ADJUSTABLE DEVICE

(75) Inventors: Robert C Baylis, Bristol (GB); David R McMurtry, Dursley (GB)

(73) Assignee: Renishaw PLC, Gloucestershire (GB)

( * ) Notice: Subject to any disclaimer, the term of this patent is extended or adjusted under 35 U.S.C. 154(b) by 135 days.

(21) Appl. No.: 10/853,293

(22) Filed: May 26, 2004

(65) Prior Publication Data

US 2005/0135874 A1   Jun. 23, 2005

Related U.S. Application Data

(63) Continuation-in-part of application No. PCT/GB02/05341, filed on Nov. 27, 2002.

(30) Foreign Application Priority Data

Nov. 27, 2001 (GB) ............................ 0128360.5
Jan. 16, 2002 (GB) ............................ 0200925.6

(51) Int. Cl.
*F16D 1/12* (2006.01)
*F16M 11/14* (2006.01)
*G01N 1/28* (2006.01)
*G01N 37/00* (2006.01)
*G02B 7/00* (2006.01)

(52) U.S. Cl. .................. 73/864.91; 73/863; 250/491.1; 403/53

(58) Field of Classification Search .................. 403/53, 403/76; 73/863, 864.91; 250/491.1
See application file for complete search history.

(56) References Cited

U.S. PATENT DOCUMENTS

| | | | |
|---|---|---|---|
| 2,895,314 A | 7/1959 | Helm | |
| 4,070,011 A | 1/1978 | Glesser | 269/45 |
| 4,141,225 A * | 2/1979 | Varner | 464/156 |
| 4,254,638 A * | 3/1981 | Dressel | 464/154 |
| 4,402,481 A | 9/1983 | Sasaki | 248/282.1 |
| 4,407,277 A * | 10/1983 | Ellison | 602/39 |
| 5,013,325 A * | 5/1991 | Rennerfelt | 623/38 |
| 5,419,522 A | 5/1995 | Luecke et al. | 248/288.51 |
| 5,536,070 A * | 7/1996 | Lemmen | 297/411.37 |
| 5,961,516 A | 10/1999 | Graf | |
| 6,179,262 B1 | 1/2001 | Ellard et al. | |

(Continued)

FOREIGN PATENT DOCUMENTS

DE   196 01 248 A1   7/1996

(Continued)

*Primary Examiner*—Thomas P. Noland
(74) *Attorney, Agent, or Firm*—Oliff & Berridge, PLC (57) ABSTRACT

An adjustable device is disclosed comprising two relatively re-orientatable members each having a lockable universal joint, and a connecting member for connecting the two relatively re-orientatable members whereby when the two relatively re-orientatable members are connected the two joints are in mechanical communication via the connecting member. The two lockable joints may be locked and unlocked using an actuator, a lever, which may act on a compression device in order to render the lockable joints either mobile or locked. The compression device may cause a change in cross-sectional area of the tube over at least a part of its length. At least one of the lockable universal joints may provide for linear movement between the two relatively re-orientatable members. Also disclosed is an apparatus for the simulation of the orientation of a sample with respect to a cutting tool or scanning probe and method for aligning the adjustable device.

21 Claims, 8 Drawing Sheets

U.S. PATENT DOCUMENTS

| | | | |
|---|---|---|---|
| 6,203,548 B1 * | 3/2001 | Helland | 606/105 |
| 6,626,904 B1 | 9/2003 | Jammet et al. | |
| 6,653,825 B2 * | 11/2003 | Munniksma | 324/72.5 |
| 7,118,601 B2 * | 10/2006 | Yasui et al. | 403/53 X |
| 2002/0122178 A1 | 9/2002 | McMurtry et al. | 356/401 |
| 2004/0202506 A1 * | 10/2004 | Lazic et al. | 403/97 |

FOREIGN PATENT DOCUMENTS

| | | |
|---|---|---|
| EP | 0 417 566 A1 | 3/1991 |
| EP | 1 072 228 A1 | 1/2001 |
| SU | 992132 A * | 2/1983 |

* cited by examiner

ADJUSTABLE DEVICE

CROSS-REFERENCE TO RELATED APPLICATION

This application is a continuation-in-part of International Application No. PCT/GB02/05341 filed on 27 Nov. 2002 and published under the number WO03/046430.

BACKGROUND OF THE INVENTION

1. Field of the Invention

This invention relates to an adjustable device and in particular to an adjustable device which can be temporarily and rigidly secured in a position.

2. Description of Related Art

It is known to provide rigid and releasable positioning devices, an example of one such device comprises a metal base member having a hollow formed therein and a metal hemisphere adapted to fit the hollow. One of the base member and the hemisphere are magnetised thus, when the hemisphere is located in the hollow within the base member, it is fixed in position. If the hemisphere is manually moved with respect to the base member, then the orientation and angle of the flat surface of the hemisphere changes with respect to the base member. Thus, if an article were placed on the flat surface of the hemisphere, the orientation and angle of this article is changed with respect to the base member as a result of this movement.

The accurate positioning of articles is required in a number of situations. One situation is where the article is to be measured to produce a mould or a direct copy of the article. In order for accurate data regarding the three-dimensional structure of the article to be obtained, the entire surface of the article must be available for measurement by, for example, a probe. Therefore, the article must be positioned so that the underside of any overhanging regions may be measured to ensure that there are no re-entrant points.

An article where re-entrant points can occur is a tooth. It is desirable to obtain information which details the exact shape and configuration of a tooth as this information can be used to produce a copy of the tooth which can replace a damaged tooth as obviously, if a crown or bridgework is made from a replica tooth it is likely to be a better fit and will also feel more comfortable to the person receiving the new dentalware.

Another situation where accurate positioning is required is when directing a light beam from a source to a reflector and subsequently a detector. An example is in a laser interferometer where the relative movement of two objects may be measured. It is important that the light beam is detected at all times during the measurement process thus the alignment of the reflector with respect to the light source and detector must be maintained.

SUMMARY OF THE INVENTION

Accordingly, a first aspect of the invention provides an adjustable device comprising two relatively re-orientatable members each having a lockable universal joint; and a connecting member for connecting the two relatively re-orientatable members whereby when the two relatively re-orientatable members are connected the two joints are in mechanical communication via the connecting member.

Preferably, at least one of the lockable universal joints comprises a tube and a joint part capable of being housed in the tube whereby the tube provides for linear movement between the two relatively re-orientatable members.

Devices according to the invention provide a six axis gimbal with one angularly rotatable connecting member between the relatively re-orientatable members for example, a base and a platform or a machine socket and a reflector housing. This has the advantage that it is rigid and potentially less likely to fail due to the reduced number of connections compared to convention six axis gimbals.

Preferably, the two lockable joints are in the form of ball and socket joints.

The tube may directly connect the balls of each lockable joint or each ball may be connected to a respective one of the relatively re-orientatable members whereby the ends of the tube provides the two sockets.

Preferably, the two lockable joints are locked and unlocked using an actuator.

In a preferred embodiment, the actuator acts on compression means in order to render the lockable joints either unlocked or locked.

The compression means can work in a number of ways, it can reduce the cross sectional area of the tube at one end, both ends or, it can act along the whole length of the tube to enable the relatively re-orientatable parts to move with respect to one another. Thus the compression means causes a change in cross-sectional area of the tube over at least a part of its length.

According to a second aspect of the invention there is provided an apparatus for the simulation of the orientation of a sample with respect to a cutting tool or scanning probe comprising:
  a stand having a base portion and at least one alignment aid; and
  an adjustable device, the adjustable device comprising a base and a relatively re-orientatable platform onto which a sample may be placed, the base and platform being connectable by two lockable universal joints when the two relatively re-orientatable members are connected the two joints are in mechanical communication via a tube wherein,
  the base of the adjustable device is locatable adjacent the alignment aid and when so located, the orientation of a sample with respect to a cutting tool or scanning probe is simulated.

Preferably, the stand further comprises a back portion having the at least one alignment aid attached thereto.

In a preferred embodiment, the apparatus is provided with a magnifying glass to aid in the exact positioning of an article with respect to the at least one alignment aid.

According to a third aspect of the invention, there is provided a method of positioning a sample prior to scanning the surface of said sample comprising the steps of:
  (a) providing a stand having at least one alignment aid;
  (b) placing an adjustable device adjacent the alignment aid, the adjustable device comprising a base and a relatively re-orientatable platform onto which a sample may be placed, the base and platform being connectable by two lockable universal joints whereby when the two relatively re-orientatable members are connected the two joints are in mechanical communication via a tube;
  (c) attaching a sample to the platform of the adjustable device;
  (d) unlocking the two universal joints;
  (e) adjusting the platform with respect to the base of the adjustable device to align the sample with the at least one alignment aid; and (f) locking the two universal joints to retain the platform in the alignment position wherein steps (b), (c) and (d) may be carried out in any order.

There are a number of ways in which the surface profile of an article can be scanned. A preferred method is where the scanning device is either a laser or LVDT (linear vernier displacement transducer) and there is rotation of the article with respect to the scanning device contemporaneously with relative vertical displacement of the scanning device and article. In such a scanning device there is a working volume in which the scan must be carried out either for reasons of accuracy or, as defined by the limits of motion of the scanning device.

According to a fourth aspect the invention comprises an apparatus for lining up components in an optical system whereby the optical system comprises a light source; a reflector; and a detector for detecting light from the light source which has been reflected by the reflector, the apparatus including an adjustable connector comprising two relatively re-orientatable members connectable by two lockable universal joints when the two relatively re-orientatable members are connected the two joints are in mechanical communication via a tube for connecting the reflector to an object which is relatively movable with respect to the light source.

The adjustable connector is capable of being actuated between a first position whereby the adjustable connector is fixed in position with respect to the object and a second position whereby the adjustable connector is movable with respect to the object. This enables the reflector attached via the adjustable connector to the object to be lined up with the light source and detector.

The light source and detector may be separate components or combined within one housing. The reflector may be a mirror or a retroreflector. A more detailed discussion of an optical system using an adjustable connector is disclosed in co-pending application US 2002-0122178 incorporated herein by reference.

BRIEF DESCRIPTION OF THE DRAWINGS

Embodiments of the invention will now be described, by way of example, and with reference to the accompanying drawings in which:

FIG. 2c shows an exploded view of the device of FIG. 2a;

DESCRIPTION OF PREFERRED EMBODIMENTS

Figure 1:
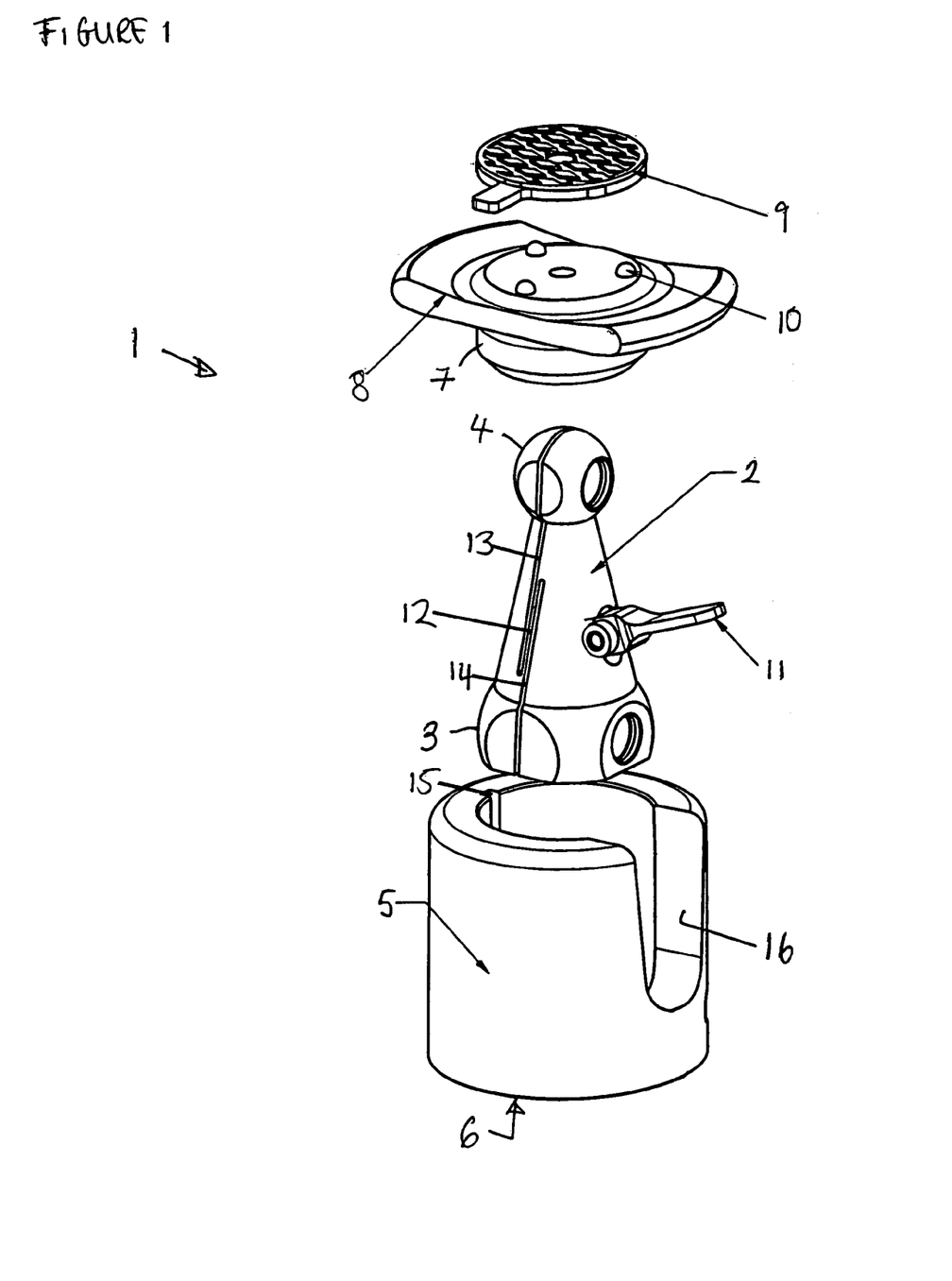
FIG. 1 shows an exploded view of a device according to the invention.

FIG. 1 is an exploded view of a device 1. The device 1 comprises an elongate body 2 having first and second ends which describe part-spherical shapes 3, 4 respectively. This elongate body and ends can be described as a connector. A first retainer 5 is cup-shaped, on one side, to house the first end 3 and the opposite side forms a base 6. A second retainer 7 is cup-shaped, on one side, to house the second end 4 and on the opposite side forms a pivotable or adjustable platform 8. A mount 9 onto which an article may be attached, is kinematically located 10 on the platform 8. A lever 11 has an over-center mechanism to actuate a planar spring 12 which is orientated longitudinally with respect to the elongate body. The first retainer 5 further comprises a first slot 15 adapted to receive a spur (not shown) which extends from the first end 3 of the elongate body 2 and a second wider slot 16, approximately diametrically opposite the first slot 15, to accommodate the lever 11.

The elongate body 2, has a normal or uncompressed state in which the ends 3, 4 have a cross sectional area which is the same as or greater than the retainer 5, 6 in which it can be housed. Thus, in this normal state, the two ends of the elongate body are rigidly received and gripped within the respective retainer thus locking the respective positions of the two retainers 5, 6. The elongate body 2, has a second or compressed state in which the ends have a cross sectional area which is less than the retainer 5,6 in which it can be housed. Thus in this second state, the two ends of the elongate body are moveable within their respective retainers.

The elongate body 2 is essentially in two parts which are connected by the planar spring 12. The planar spring is formed between two slots 13,14 which occur through the thickness of the elongate body 2. Each slot begins from a respective end of the elongate body and runs past the center of the length of the elongate body thus providing a central or bridge region in which both the slots occur, the area between the slots in this central region comprising the planar spring. A planar spring allows the compression action to be achieved over the whole length of the elongate body by the introduction of only one spring. The bridging region also conveniently provides a rigid shear connection between the two parts of the elongate body.

An adjustable device as hereindescribed is suitable for the positioning of articles in preparation for scanning the surface of those articles. The mount 9 onto which an article, for example, a dental part is secured may be moved into a number of different orientations and positions enabling different aspects of the article to be viewed. Once a suitable position for the dental part is obtained, the adjustable device can be temporarily secured in that position ready for a scan of the surface of the dental part.

When the article is said to be secured to the mount, this may be achieved in a number of ways and the article can be either removably or permanently secured. The method of securing is dependent on the purpose for which the article is being secured and the conditions that the article will be subject to. Examples of different ways to secure the article include using cement, glue, putty or gum although others will be apparent to the person skilled in the art. The mount may then be attached to the platform in a releasable manner for example, by magnets, kinematically, or by a more permanent manner such as gluing.

In order to assemble the parts of the device shown in FIG. 1, the lever 11 is actuated causing compression of the planar spring 12. This results in a reduction in the cross sectional area of the elongate body 2 along its length enabling the part-spherical ends 3,4 to be housed within the retainers 5,6 respectively. In this compressed state, the elongate body can be manipulated in order to obtain the desired orientation and angle of the pivotable or adjustable platform 8 with respect to the base 6. Once the desired position is achieved, the lever 11 is actuated to uncompress the spring, which results in the elongate body returning to its normal state i.e. its cross sectional area increases back to its original or normal size and the ends of the elongate body are locked in that position.

The slot 15 and spur (not shown) that extends from the first end 3 of the elongate body ensure that an article held on the platform is not rotated in the plane of the platform i.e. the spur locates the first end with respect to the first retainer. The slot 15 further ensures that the lever 11 is centered in the wider slot 16 which accommodates the lever 11.

The device shown in FIG. 1 has a first retainer 5 of significantly greater depth than the first end of the elongate body 2. This enables the height of the device to be adjusted as well as the angle and orientation of the platform. The person skilled in the art will appreciate that increasing the height of the device beyond a point at which the surface area of contact between the end of the elongate body and the retainer begins to decrease can lead to unstable securing of the position of the platform and, that in reducing the height such that the end of the elongate body is below the edge of the retainer within which it is received will result in reduced angular movement.

Height adjustment is also facilitated by the wider slot 16, which accommodates the lever 11 as it allows the height of the device to be reduced beyond the point at which the lever 11 protrudes from the elongate body 2. The slot 16, if wider than the diameter of the elongate body 2, may allow the elongate body 2 to tilt further when the elongate body is pivoted towards the slot enabling a greater degree of movement in this direction. This is because the slot accommodates the elongate body 2 allowing the elongate body to pass through the wall of the first retainer 5.

Whether the platform is considered pivotable or adjustable with respect to the base 6 depends on, amongst other things, the relative movement of each end 3, 4 of the connecting portion of the device 1 within their respective retainers 5, 7.

Figure 2A:
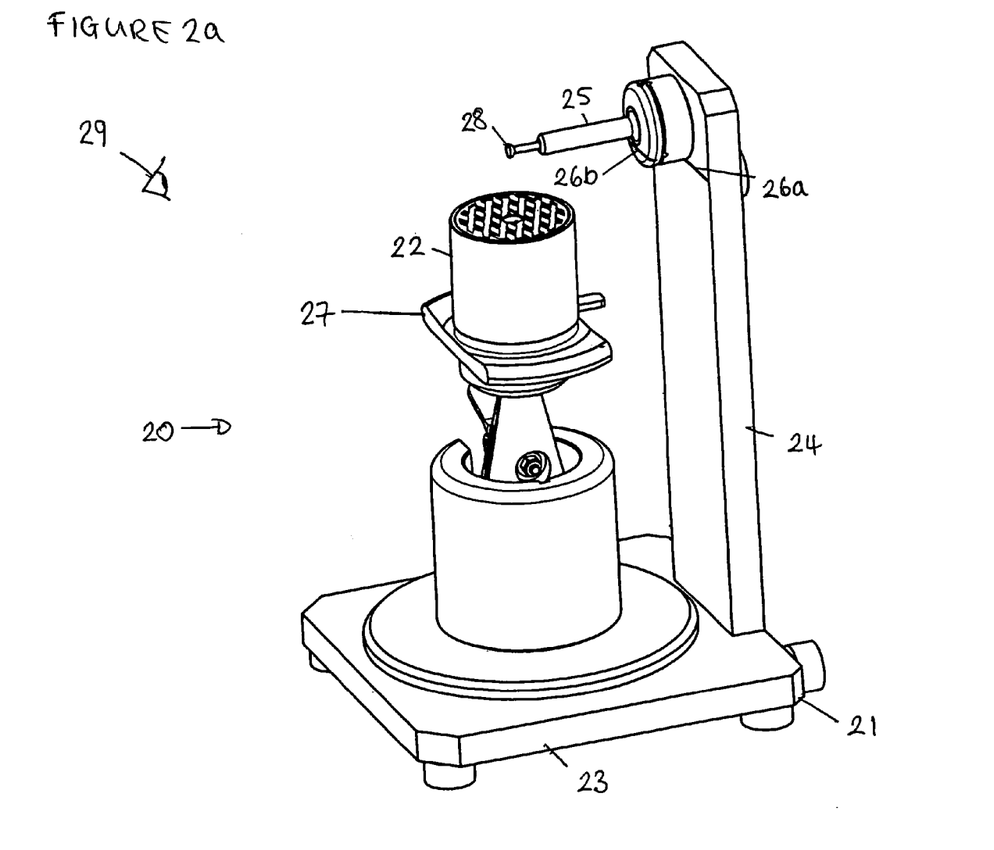
FIGS. 2a and 2b show isometric views of a device according to the invention mounted on a stand.
Figure 2B:
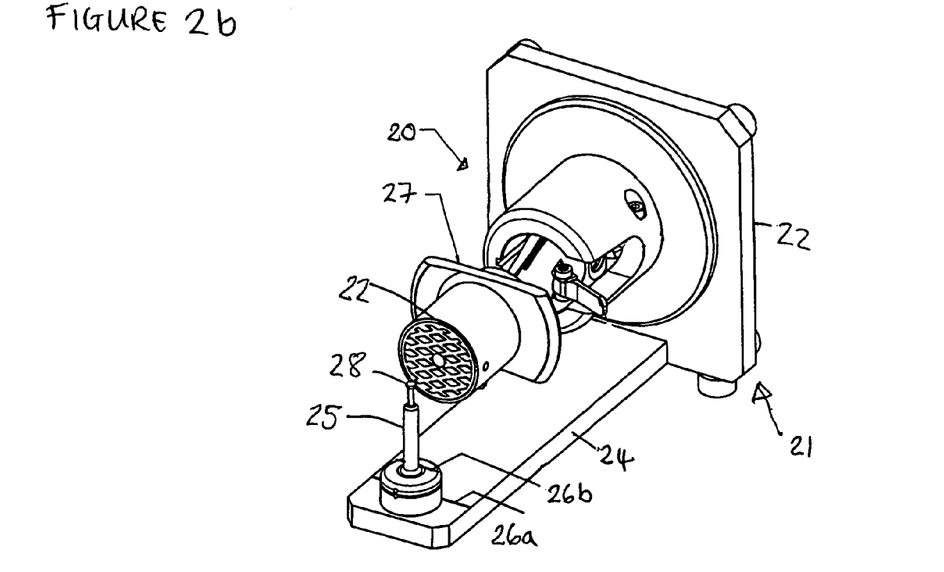

FIGS. 2a and 2b show a device 20 mounted on a stand 21. The device 20 incorporates a supplementary article mount 22 positioned on top of the pivotable or adjustable platform 27. The stand has a base portion 23 and a back portion 24 which extends substantially perpendicularly to the base portion. Alignment aids 25, 26 are attached to the back portion 24 at a distance from the base portion 23 which is determined by the required height of the platform 27 or article (not shown) mounted thereon for example, for the performance of a scan of the surface of the article. One alignment aid 25 is a projecting rod or element having a tip 28. The other alignment aid 26 is a stripe having two portions 26a and 26b having different heights from the back portion 24 of the stand.

The stand 21 can rest on either the base portion or the back portion depending on which alternative provides the easiest view of the article to be positioned.

The first alignment aid 25 is a projecting rod having a tip 28. The first alignment aid projects from the stand substantially parallel to the base portion 23 the stand and positioned adjacent the adjustable device at a height which is determined by the desired height for either the platform 27 or an article placed on the platform. When there is an article on the platform, the alignment aid can be used to ensure that there are no re-entrant points on the article when it is fixed in a certain position or, in the case of a scan of an internal surface, that the probe can access the cavity. This is achieved by comparing a side of the article with the projecting rod. For accurate vertical positioning, the tip may be placed so that it touches the upper surface of a correctly positioned article. The tip 28 is at the center of a circle described by the base of the device. Thus, the alignment aid 25 may be used to position an article on the device 20 in terms of height and the center of the circle defined by the base of the device.

The tip 28 should be of the same order of size as the tip of a contact scanning device or of the smallest acceptable re-entrancy. If a re-entrant point is detected, then the position of the tooth model may be altered by actuation of the lever 11 which enables relative movement of the platform 27 with respect to the base 6, 23. The tooth model is then rechecked for re-entrancy.

Figure 2C:
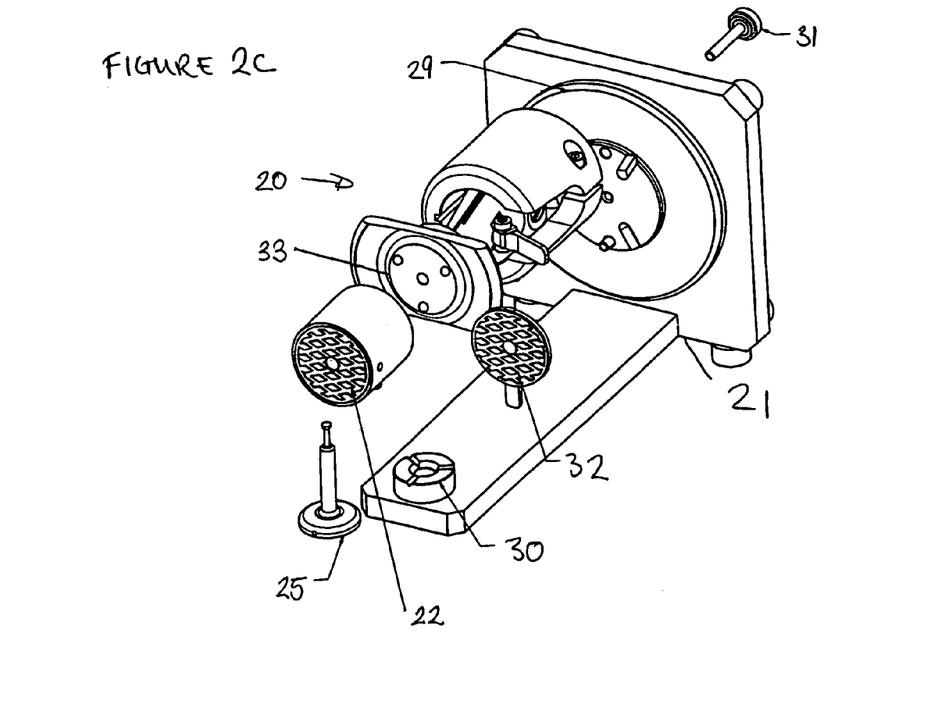

The second alignment aid 26 is a stripe across the base of the projecting rod having two regions 26a and 26b. Region 26a is on the back portion 24 of the stand and region 26b is at a height of 0.5 cm above it. This height differential allows a person to repeatedly position their eye 29 in the same location with respect to the first alignment aid 25. This is when no parallax is seen between the two stripe regions 26a and 26b. The stripe may be of any colour which provides sufficient contrast against both the back portion of the stand and the base of the projecting rod so, enabling both regions of the stripe to be seen. FIG. 2c shows an exploded view of the device shown in FIGS. 2a and 2b. The device 20 and the alignment aid 25 are secured to the stand 21 via kinematic location 29, 30 respectively. This enables accurate repositioning on the stand of both the device and alignment aid following removal from the stand. To further secure the device 20, a mounting screw 31 may be used to attach the device to the base. A mount 32 or a supplementary article mount 22 is also kinematically located 33 on the platform 27.

A stand with an alignment aid is particularly useful when trying to position an article for scanning. This is because the alignment aid enables accurate positioning of an article placed on the platform in all three dimensions. The person skilled in the art will appreciate that the device is at its most stable when the platform (and thus an article) is located perpendicularly above the base of the device. The tip of an alignment aid can thus be positioned not only at the correct height for the upper surface of an article to be scanned but also so that it is at the center of the circle described by the base of the platform and advantageously, the working volume of the scanning device.

The alignment aid may also be secured to the stand magnetically or kinematically 33. This is particularly useful if a set of articles of similar dimensions, for example teeth, are to be repeatably positioned, as it ensures that the alignment aid is placed at the correct distance from the base of the adjustable device. It also means that the alignment aid can be temporarily removed to assist when removing or placing a device on the stand or, when securing an article to the device.

Figure 3:
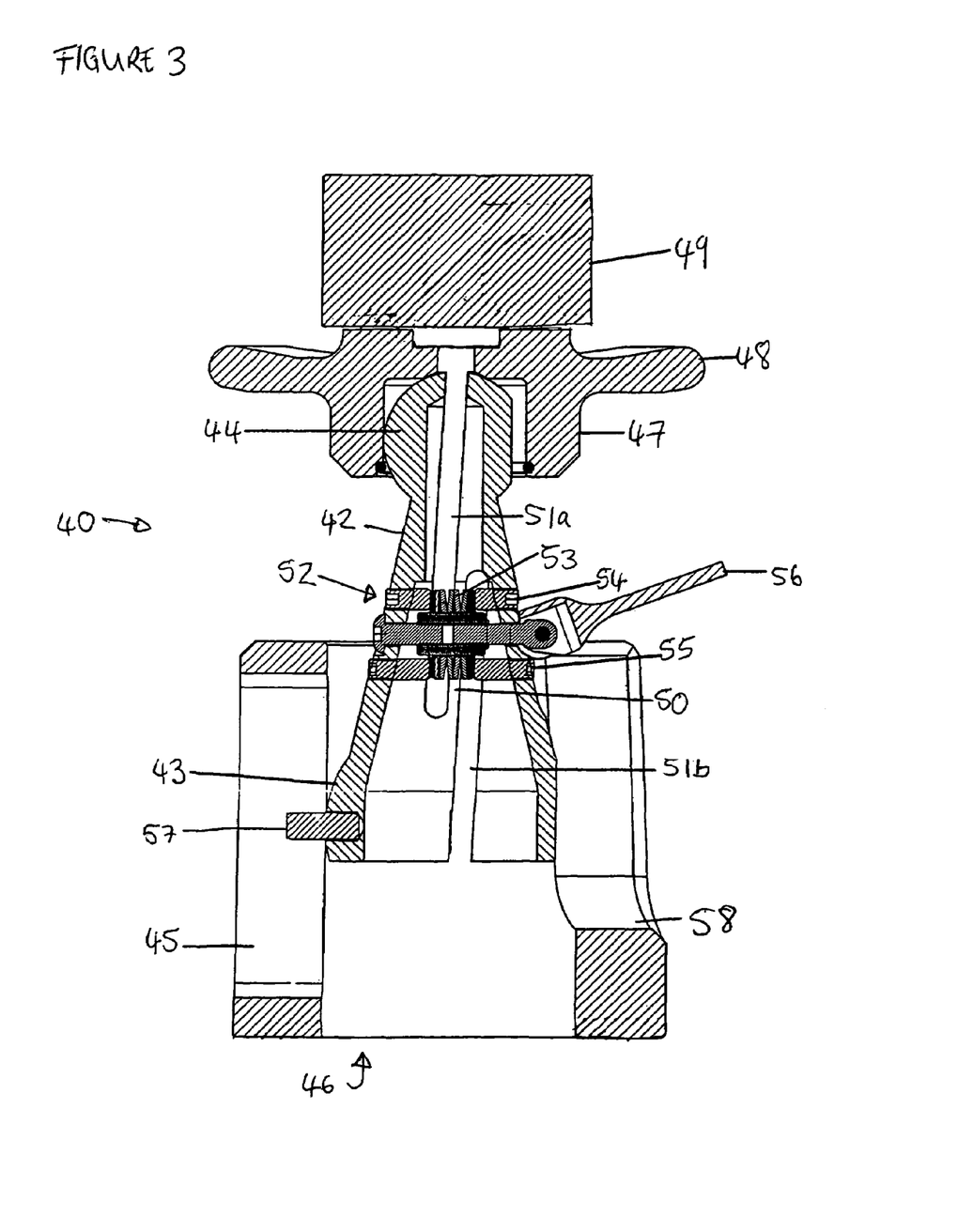
FIG. 3 shows a cross section of a device according to the invention.

FIG. 3 shows a cross section through a device 40. The device comprises an elongate body 42 having first and second ends which describe part-spherical shapes 43, 44 respectively. A first cup-shaped retainer 45, having a base 46, houses the first end 43. A second cup-shaped retainer 47, forms a platform 48 and houses the second end 44. A mount 49 onto which an article may be secured, is located on the platform 48. A planar spring 50 is formed between two halves of the elongate body 42 where two slots 51*a*, 51*b* each beginning from a respective end of the elongate body overlap in the central region of the elongate body 42. In this central region, a further compression means 52, is provided. This further compression means 52, has a number of pairs of Belleville washers 53 with an outer flat washer (not shown), one placed on each end of the Belleville washers. A pair of flat headed grub screws 54, 55 act on the flat washers (not shown) and are adjustable from the outside of the elongate body 42. A lever 56 has an overcenter mechanism to actuate the further compression means 52 and the planar spring 50. A spur 57 that extends from the first end 43 of the elongate body 42 is located in a slot (not shown) within the first retainer 45. A second slot 58 in the first retainer 45 is located substantially diametrically opposite the first slot (not shown).

When the lever 56 is actuated, the Belleville washers 53 are flattened. This forces the slots to compress resulting the cross sectional area of the elongate body 42 being reduced. Thus, this biasing means acts through the thickness of the elongate body. The ends 43,44 of the elongate body 42 can be freely moved within the retainers 45,47 enabling the repositioning of the platform 48 with respect to the base 46. When the repositioning is complete, the lever 56 is returned to its first position, this releases the pressure on the Belleville washers allowing the slots to reopen causing the cross sectional area of the elongate body 42 to revert to its normal state, retaining the ends 43,44 of the elongate body 42 in the repositioned orientation.

The further compression or biasing means may comprise a compression spring located one at each end of the elongate body as an alternative or in addition to a centrally located compression spring. If such biasing means are provided, a more distinct boundary between the point at which the ends of the elongate body are retained or released within the retainers can be achieved. This can prevent accidental movement of the ends of the elongate body within the retainers prior to them being rigidly secured within the retainers.

The pair of flat headed grub screws 54,55 enable the cross sectional area of the elongate body 42, to be adjusted. This means that the ends 43,44 of the elongate body 42 can be accommodated and retained in retainers having slightly different sizes due to wear of the device or variations during manufacturing.

An alternative embodiment of the connector will now be described with reference to FIG. 4. A first retainer 60 houses a first ball 62 of the adjustable connector within a socket. At the distal end of the connector is second ball 70 which is connected by a tube 78 to the first ball 62. The second ball 70 lies inside the bore 68 of a second retaining device 66.

The balls 62 and 70 of the adjustable connector may only have a part spherical surface at the portion of the ball in contact with the surface of the bore, which in this case is cylindrical.

The first ball 62 can be adjusted through a limited angle with respect to the tube to enable it to be engaged in the socket 64 of the first retainer 60. The ball is retained in socket 64 in known manner by providing magnets (not shown) in the ball 62, the socket 64 or both.

Two slits 74,76 extend from opposite ends of the adjustable connector along its longitudinal axis to just short of its center, leaving just a small bridging portion 78 connecting the two portions of the adjustable connector together. A locking screw 80 is provided in the first retainer 60 which when tightened pushes against the ball 62, thus fixing the ball 62 within the socket 64 and also pushing the two halves of the ball 62 together. The bridging portion 78 of the adjustable connector acts as a hinge and as the two halves of ball 62 are pushed together, the two halves of ball 70 are pushed apart and against the sides of the cylindrical bore 68, fixing it in position. This connector thus has the advantage that one actuation locks both balls.

An example of a use for such a connector is in lining up parts of an optical measuring system. In such an optical system, light must be directed from a source onto a reflector which is attached to a relatively movable object and back to a detector. In order that the light is detected, the reflector must be accurately aligned to the detector. An optical measuring system may be used in the calibration of machines with relatively movable parts for example a coordinate measuring machine (CMM) or machine tool where a probe or tool is movable within a working volume. For a calibration process, a reflector would be attached to a machine spindle in place of the probe or tool and the movement of the spindle checked for accuracy, alignment and other geometric errors.

Once a source housing is correctly aligned to direct a light beam along, for example, one of the machine axes, e.g. the X-axis, a reflector housing can be seated on a kinematic seat on the front face of the source housing, and will automatically be aligned with the beam from the light source and the detector. Magnets are used to urge the two housings together at the kinematic seat.

In order to take care of any mis-match in position between a machine spindle 60 and the reflector housing 82, whilst retaining alignment with the source, the reflector housing is provided with a limited amount of compliance by using the adjustable connector by means of which the housing can be connected to the spindle of the machine.

The reflector housing 82 is connected to the adjustable connector via a kinematic seat 72 on the second retainer. The first retainer 60 is either attached to a machine spindle, or conveniently is the machine spindle which enables direct connection between the machine spindle socket 64 and the first ball 62 of the connector.

Once the source housing (not shown) has been aligned with an axis of the machine, the reflector housing 82 attached to the machine spindle can be brought up to the source housing. With the locking screw 80 loosened, the adjustable connector will be free enough to rotate so that the reflector housing 82 will seat in the kinematic seat with the source housing. By this means automatic alignment of the source housing and the reflector housing 82 can be ensured. Once seated in the kinematic seat the locking screw is tightened to maintain the orientation of the housing 82.

It is desirable to be able to align the source housing with other machine axes. In the above-described example, the source housing is ideally kinematically mounted on a base plate. The source housing may then have other sets of kinematic elements on its lower surface or on other ones of its orthogonal faces. By this means it can be rotated through 90° in different planes and be re-seated on the kinematic seat on the base plate in different orientations with the light beam from the source directed along different machine axes. The reflector housing will continue to seat in the same kinematic seat 18 on the source hosing so that it will also be aligned with the different axes.

Figure 4:
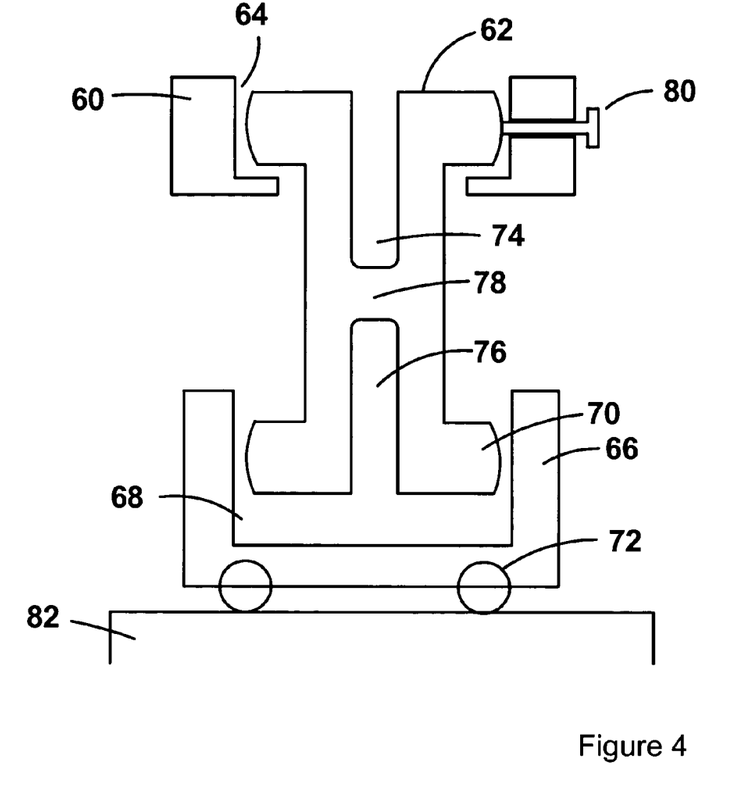
FIG. 4 is a side view of an alternative device according to the invention.
Figure 5:
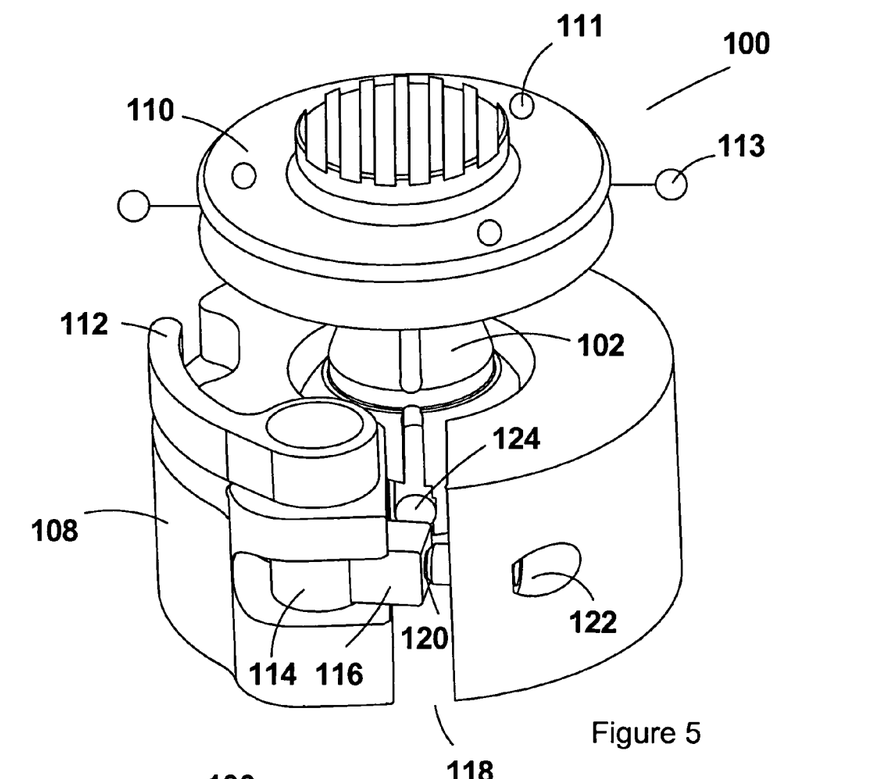
FIG. 5 is an isometric view of a device according to the invention.
Figure 6:
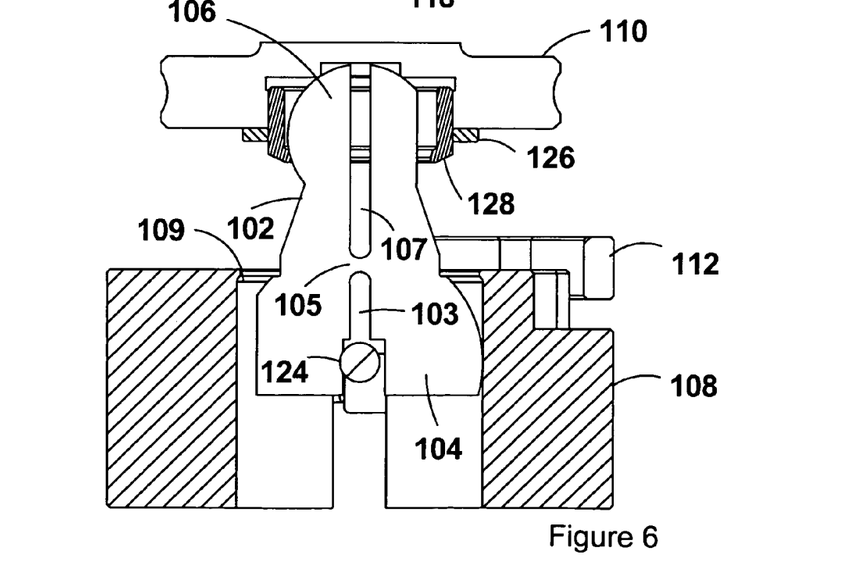
FIG. 6 is a cross-sectional view of the device shown in FIG. 5.

FIGS. 5 and 6 show a device 100 having a connector 102 which is of similar design to that shown in FIG. 4. The connector 102 has an elongate body with part spherical end portions 104,106 and two longitudinal slits 103, 107 of different lengths which lie on the longitudinal axis of the connector and are separated by a bridge portion 105. Thus the bridging portion is substantially perpendicular to the longitudinal axis of the elongate body. The part spherical end portions do not have the same diameter. The larger of the two end portions 104 is releasably retained in a base 108 which incompletely encircles and houses the larger end portion i.e. there is a gap 118 in the circumference of the base.

The smaller of the two end portions 106 is releasably retained in an underside recess of a platform 110 onto which an object (not shown) may be mounted. A lever 112 may be actuated between two positions open when the connector 102 is movable with respect to both the platform 110 and the base 108, and closed (as shown in the drawings) when the end portions 104, 106 of the connector are retained within the base 108 and platform 110 respectively. The orientation of the platform with respect to the base is fixed in this retained position until the lever 112 is moved to the open position at which point, the respective orientations may be changed.

The method of operation will now be explained. The lever 112 is connected to a shaft (not shown) on which bearings are mounted. A central bearing 114 (it will be appreciated that a minimum of three bearings are required) has an eccentric diameter, so is offset for at least a part of its circumference compared to the other bearings. An extension piece 116 rests against the central bearing 114 and protrudes into the gap 118 in the base 108. On the end of the extension piece 114 is a small concavity in which is secured a correspondingly sized ball bearing 120. The ball bearing and extension piece are held in position across the gap by a grub screw 122 which protrudes from the opposite wall of the base which defines the gap 118. Thus the extension piece 114 and ball bearing 116 rest against two surfaces and bridge the gap 118.

It is preferred that diametrically opposite gap 118 is provided a waisted portion in the base which provides a hinge point for movement of the device between lever open and lever closed positions.

When the lever 112 is in its closed position (as shown), the diameter of the base 108 is at or near its smallest thus, in this position, the end portion 104 is retained in the base 108 and, by an opposite reaction to the compression of the end portion 104 held in the base 108, the smaller end portion 106 is expanded within the underside recess of platform 110 resulting in both ends of the connector 102 being locked into position.

As the lever 112 is moved into the open position, the shaft and bearings rotate and as this occurs the eccentric part of the central bearing 114 begins to engage with the extension piece 116 which causes more force via the ball bearing 120 on the grub screw 122. This causes the base 108 to increase in diameter until the maximum of eccentricity is reached.

The larger end portion 104 is thus gradually uncompressed until it can freely move within the base 108 and by the hinge action of the bridge portion 105, the smaller end portion 106 gradually reduces in diameter until it is free to move with respect to the platform 110.

In order to locate the connector 102 with respect to the base 108, a spur 124 may be provided, for convenience during manufacture, this is located in the slit 103 which runs through the larger end portion 104. One way to locate the spur within the slit 103 is to secure it using a cap screw and a pair of locating points on a wall of the slit 103. The locating points could be formed by a recess in the wall.

In a preferred device, the extension piece 116 and the larger and smaller sizes of the gap 118 are designed such that once the connector is released, the extension piece toggles overcenter maintaining the connector in the released state until a positive action occurs. The size of the gap may be adjusted using the grub screw 122. In this preferred device, the ball bearing 120 acting on the grub screw 122 acts like a pivot.

As an aid to a person who is trying to position the platform 110 with respect to the base 108, the lever 112 may include a tension spring which allows the lever to return to near the closed position, about 200 from the closed position is ideal, ready for fixing the connector with respect to the base and platform with a small tap by a finger on the lever. One way on achieving this is by providing the toggling feature and allowing the lever to move independently of at least the central bearing 114 towards the return position, without disengaging the toggle, under the bias provided by the tension spring. One way to do this is to have one or more slots in the hub of the lever in which rides a stop attached to the shaft thus allowing movement of the lever over the range of the slot prior to engagement of rotation of the shaft and bearings.

If advantageous, the motion of the lever back towards the closed position could begin to cause retention of the end portions within their respective housings and so restricting the motion of the end portions within the housings. This would enable fine tuning operations of the position of the platform with respect to the base to be carried out using only one hand.

Although the connector shown in FIGS. 5 and 6 is of a similar design to that of FIG. 4, there are a few differences as the balls of FIG. 4 are of substantially similar size and the bridging portion is at the approximate mid-point of the connector. These modifications result from the circumstances in which the connectors may be used.

Referring now to FIG. 6, in order to account for manufacturing tolerances, thermal expansion or merely to give an extra adjustment to that of the grub screw, the smaller end portion 106 is provided with a locking nut 126. The locking nut 126 is screwed onto the outer thread of a sleeve 128 which is a close tolerance bore that fits over the smaller end portion 106 within a cavity in the underside of the platform 110 provided to house the smaller end portion 106. By tightening the locking nut 126, the smaller end portion 106 is compressed by the sleeve 128. This causes the larger end portion 104 to expand in diameter within the base due to the hinge action of the bridging portion 105. This feature allows adjustments to be made to the diameter of the larger end portion 104 as well as the diameter of the base 108.

The use of the locking nut 126 is advantageous as it enables the larger end portion 104 to be manufactured with a smaller diameter than the internal diameter of the base 108. This ensures that the larger end portion 104 makes only three points of contact within the base when adjusted, via the locking nut, to fit the base (as long as the locking nut is not overtightened). Three points of contact are desirable, as the end portion will then sit firmly in position (no wobble).

In order to prevent removal of the larger end portion 104 from the base 108, the base is provided with a retaining lip 109 at its upper surface which reduces the diameter of the bore in which the larger end portion 104 is housed at this upper surface to a diameter which is smaller than that of the larger end portion when in its uncompressed state.

Reference features 111,113 may be provided on or associated with platform 110. These features are advantageous in a number of circumstances. For example, if the device is located in an environment which is thermally unstable and a measurement process takes place in a number of discrete steps which could take hours or even days to complete. Such a process is the production of a bridge for replacing teeth where not only does a cast of the patient's mouth have to be measured (to establish the inner bridge surface) but, also the outer surface which is traditionally manually modelled on the cast using wax, a time consuming process. The reference features may be present on the upper surface of the platform for example as hemispheres 111, recesses or colored dots. Any feature which can be recognised by the measurement device which will be used (contact or non-contact therefore). Alternatively, and particularly for the case where an elongate or large object will be placed on the platform, the reference features can protrude from the side of the platform 110 as balls on stalks 113 for example.

At least three such features are provided so the plane of the upper platform surface can be established along with axial and point information. Thus, between stages in a measurement process, the position and orientation of the platform surface can be checked enabling separate measurement steps to be aligned with each other.

Figure 7:
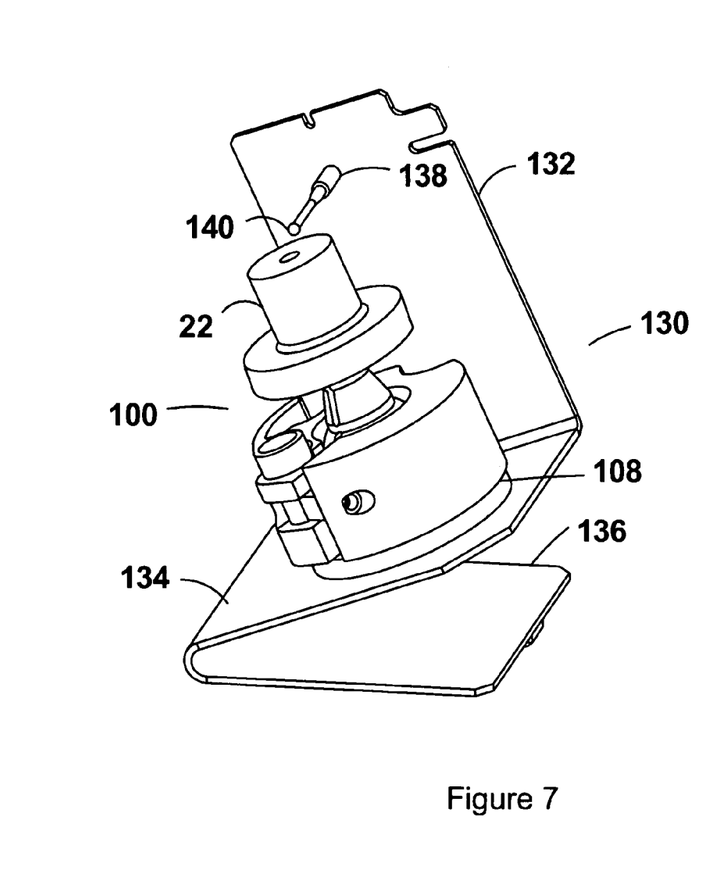
FIG. 7 shows an isometric view of a device mounted on a stand.

FIG. 7 shows an isometric view of a device 100 located on a stand 130. The stand 130 has a folded base portion and a back portion 132. The device 100 is supported on a first surface 134 of the base portion which is substantially orthogonal to the back portion 132. This first surface 134 is inclined (at about 20°) to a second surface 136 which is designed to rest on a supporting structure such as a laboratory bench. This means that the device is inclined at about 20° from perpendicular whilst supported on the stand. The back portion of the stand 132 includes an alignment aid 138 which is a projecting rod with a tip 140 and which has been described in detail with reference to FIGS. 2a, b and c.

The alignment aid 138 shown in FIG. 7 is appropriate for aligning a single tooth for a scanning process. The device includes a supplementary mount 22 in order to raise the height of a tooth positioned on the device 100 so that it is within the scanning volume of a scanner. In effect, a supplementary mount 22 enables the same device 100 to be used for the positioning of articles of differing size for the purpose of a scanning process i.e. it enables location of different sized articles within the working volume of a scanner without the need for different sized devices.

Figure 8:
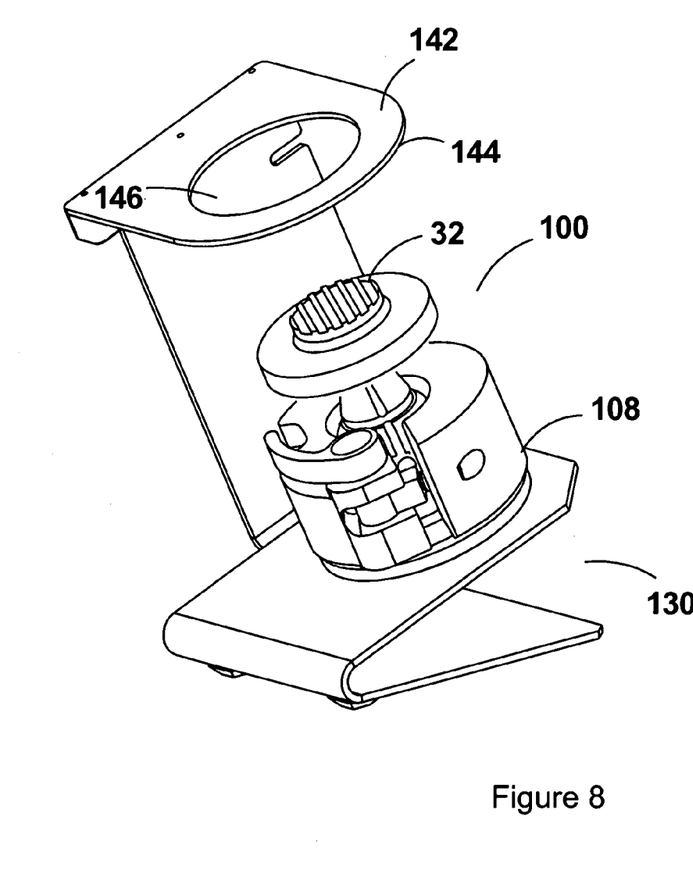
FIG. 8 shows an isometric view of a device mounted on an alternative stand.

FIG. 8 shows a stand 130 having an alternative alignment aid 142. In this case, the alignment aid comprises a setting template for positioning articles which are mounted on the device 100. The template alignment aid 142 defines a working volume in which an article must be positioned in order for a scanning process to be performed on the article by a particular scanner (not shown). The limit of the working volume is defined by an outer edge 144 of the template 142. A central portion of the template is either marked or removed 146 which defines a preferred location of the article with respect to the base 108 of the device i.e. this central portion defines the central part of the working volume of a scanner or, the working volume where the scanner is most accurate. The template is located at a height which defines the top of the working volume of the scanner and is substantially orthogonal to the first inclined surface 134 of the stand 130. Thus, a person adjusting an article on the device would look through the template or removed central portion at the upper surface of an article positioned on the device.

The template alignment aid 142 is appropriate for use with articles which are elongate or non-uniform in shape such as a jaw section for a bridge. The template is preferably transparent, made from Perspex, an acrylic or similar material. The template may have a grid pattern printed thereon to enable centering of non-uniform shapes within the working volume.

Figure 9A:
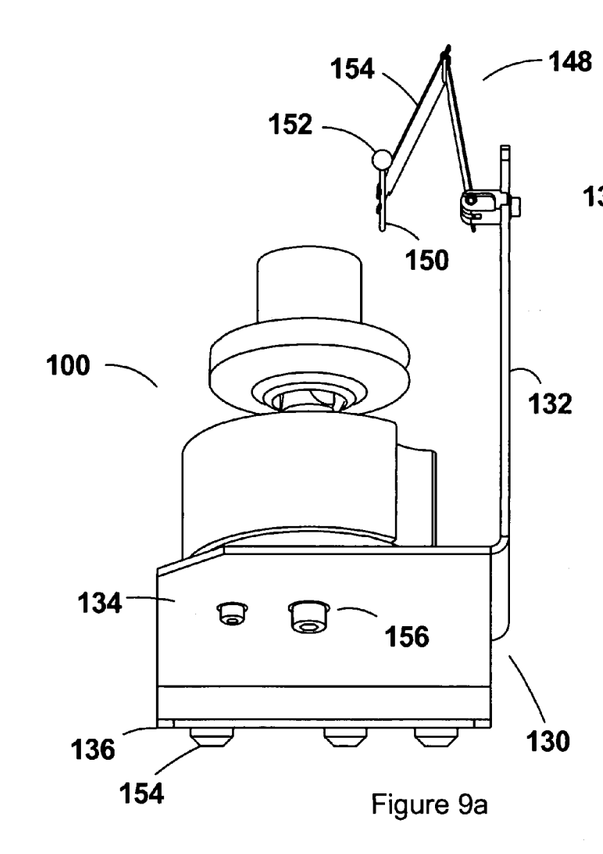
FIGS. 9a and 9b show isometric views of a device mounted on a further stand.
Figure 9B:
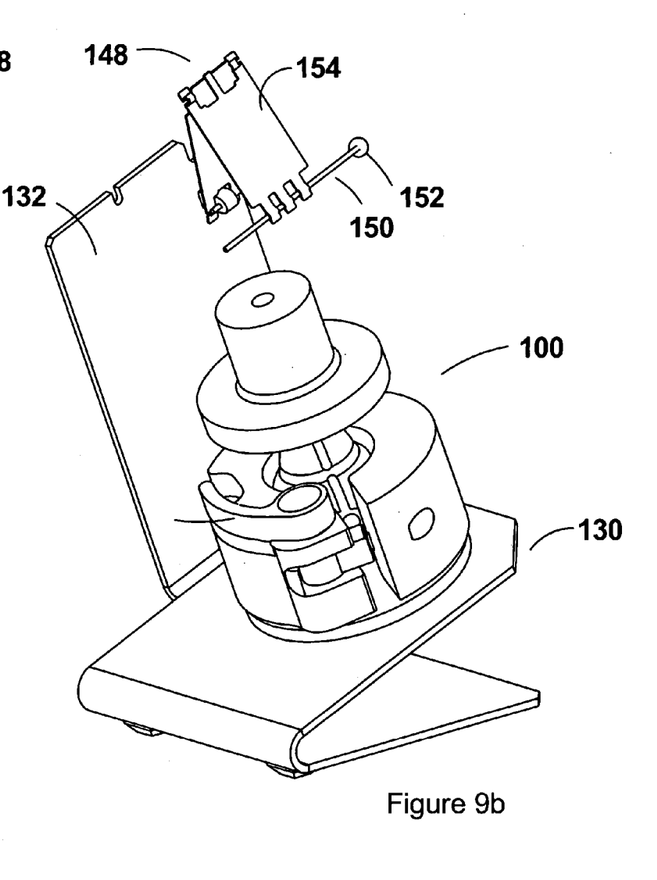

FIGS. 9a and b show a further alignment aid 148. This particular alignment aid comprises a pin 150 having a tip 152 supported on a hinged arm 154. The hinged arm 154 is rotatably mounted to the back 132 of the stand 130 and is offset from the center of a circle described by the base 108 of the device 100. The amount of this offset is a function of the size of the article whose positioning is being checked/ adjusted. The arm is hinged in two places to enable the pin 150 to be moved towards and away from the back 132 of the stand 130 and vertically with respect to the base portion of the stand 130. The pin 150 is slidably mounted on the end of the hinged arm 154.

The stand preferably has three rubber feet 154 (FIG. 9a) in order to enable the stand to sit securely on a surface.

The device 100 may be supported on the inclined surface 134 of the stand 130 in a number of ways. The device 100 and stand 130 are preferably manufactured from a metal such as aluminium or stainless steel which may be anodised. It is important that the device 100 can be accurately repositioned on the stand 130 as the alignment aids 25, 26, 138, 142, 148 associated with the stand define, either directly or indirectly, the center of the working volume of the scanning device that will be used to scan an article on the device. The device may be temporarily screwed into the inclined surface 134, or a central locating hollow may be provided in the inclined surface. Alternatively, the device 100 may merely be placed on the inclined surface of the stand 130 however, this has the possibility of movement of the base on the stand. Preferably, the device is secured on the stand magnetically. This mitigates the problem of accidental movement of the base of the adjustable device with respect to the base portion of the stand. More preferably, the device is secured on the base portion of the stand by kinematic location. This has the advantage that the device can be completely removed from the base portion of the stand, either accidentally or on purpose, and can be repositioned in exactly the same relative position to the base portion of the stand and the alignment aid.

The alignment aids herein described may assist in locating re-entrancy and, for single tooth scans an important feature called the margin line can be identified for the production of crowns. The tooth model is generally a wax replica of the exterior surface of a tooth to be crowned and an important feature is the determination of the point at which the crown will abut the gum line which is called the margin line of the tooth. The margin line is generally characterised by an increase in the diameter of the tooth followed by a subsequent decrease. The alignment aids having a tip enable the tip to track the margin line and check the tooth model for re-entrant points at this line or above it. For the production of a crown, the alignment aid having a tip is preferably attached to the back 132 approximately 5 cm below and 10 cm from the center of the working volume as this is the ideal place for the positioning of a margin line with respect to the working volume of a scanning device.

Figure 10A:
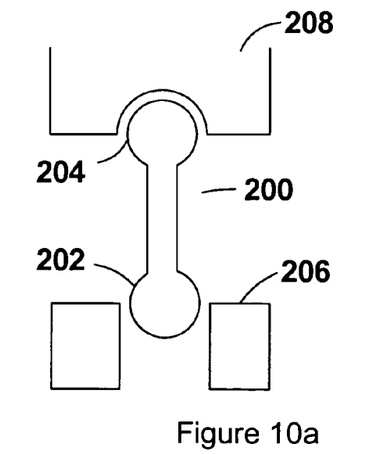
FIGS. 10a and 10b show cross-sections through alternative embodiments of the invention.
Figure 10B:
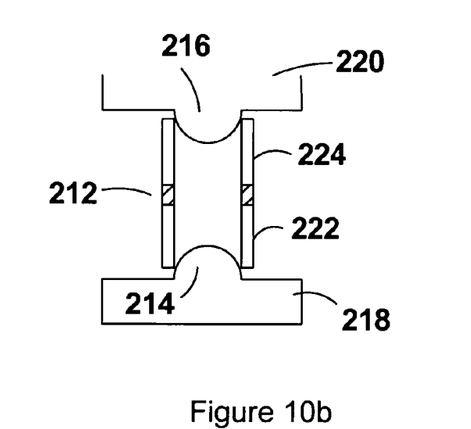

Although the invention has been described thus far as a connecting piece 200 having at least part spherical end portions 202, 204 which are housed in a tube 206 or retainer 208, the connecting piece could alternatively consist of a tube 212 into which end portions 214, 216 which are attached to a base 218, platform 220 or other object are inserted or mounted around (see FIGS. 10a and 10b respectively). The tube having a planar or flexure spring formed from longitudinal slots 222, 224 running across the diameter of the tube. In this example, two fixing actuators would be necessary (not shown).

If the connector were manufactured from two separate pieces instead of as described with an integral flexure connection then an additional shear connection would be required, such as a dowel, between the two separate pieces in order to prevent shear motion from occurring.

The invention claimed is:

1. An adjustable device comprising:
   two relatively re-orientatable members each having a lockable universal joint; and
   a connecting member for connecting the two relatively re-orientatable members, whereby when the two relatively re-orientatable members are connected the two joints are in mechanical communication via the connecting member, wherein an action of at least one of the universal joints enables linear movement between the two relatively re-orientablemembers thereby allowing the linear separation between the two relatively re-orientable members to be adjusted, wherein the two relatively re-orientatable members are lockable at each of a plurality of linear separations.

2. The device according to claim 1, wherein at least one of the two lockable joints is locked and unlocked using an actuator.

3. The device according to claim 2, wherein both lockable joints are locked and unlocked using a single actuator.

4. The device according to claim 2, wherein the actuator is a lever.

5. The device according to claim 2, wherein the actuator is a screw.

6. The device according to claim 1, wherein at least one of the lockable universal joints comprises a tube and a joint part capable of being housed in the tube whereby the tube provides for linear movement between the two relatively re-orientatable members.

7. An adjustable device comprising:
two relatively re-orientatable members each having a lockable universal joint; and
a connecting member for connecting the two relatively re-orientatable members, whereby when the two relatively re-orientatable members are connected the two joints are in mechanical communication via the connecting member,
wherein an action of at least one of the universal joints enables linear movement between the two relatively re-orientatble members,
wherein at least one of the two lockable joints is locked and unlocked using an actuator, and
wherein actuation of the actuator causes a change in cross-sectional area of the connecting member over at least a part of its length.

8. The device according to claim 7, wherein the actuator acts on compression means in order to change the cross-sectional area of the connecting member over at least a part of its length.

9. The device according to claim 7, wherein the connecting member is divided into two parts longitudinally with a rigid shear connection joining the two parts.

10. The device according to claim 9, wherein the rigid shear connection is a bridging member formed from a dowel or a bridging portion between the two parts of the connecting member.

11. The device according to claim 10, wherein the bridging member is substantially perpendicular to the longitudinal axis of the connecting member.

12. The device according to claim 11, wherein the bridging member acts as a hinge.

13. The adjustable device of claim 7,
wherein the connecting member has two elongate portions joined by a bridging member, the bridging member being substantially perpendicular to the longitudinal axis of the elongate body, and
wherein actuation of the actuator either locks or unlocks both of the lockable universal joints.

14. An apparatus for the simulation of the orientation of a sample with respect to a cutting tool or scanning probe comprising:

a stand having a base portion and at least one alignment aid; and an adjustable device, the adjustable device comprising a base and a relatively re-orientatable platform onto which a sample may be placed, the base and platform each having a lockable universal joint and, a connecting member for connecting the base and platform whereby when the base and platform are connected the two joints are in mechanical communication via the connecting member, wherein the base of the adjustable device is locatable adjacent the alignment aid and when so located, the orientation of a sample with respect to a cutting tool or scanning probe is simulated.

15. The apparatus according to claim 14, wherein the base of the adjustable device is received on the base portion of the stand.

16. The apparatus according to claim 14, wherein the stand further comprises a back portion having the at least one alignment aid attached thereto.

17. The apparatus according to claim 16, wherein the at least one alignment aid is selected from a projecting rod; a stripe having at least one region on the back portion of the stand and another region which is raised with respect to the back portion of the stand; a hinged arm; a template.

18. The apparatus according to claim 14, further comprising a magnifying glass for magnifying an article secured to the platform.

19. The apparatus according to claim 14, wherein the base of the stand comprises two surfaces inclined to one another.

20. The apparatus of claim 14, wherein the apparatus positions the sample prior to scanning a surface of the sample by:

placing the adjustable device adjacent the alignment aid;

attaching a sample to the platform of the adjustable device;

unlocking the two lockable universal joints;

adjusting the platform with respect to the base of the adjustable device to align the sample with the at least one alignment aid; and locking the two lockable universal joints to retain the platform in the alignment position.

21. An apparatus for lining up components in an optical system whereby the optical system comprises:
a light source;
a reflector; and
a detector for detecting light from the light source which has been reflected by the reflector, the apparatus including an adjustable connector for connecting the reflector to an object which is relatively moveable with respect to the light source,
wherein the adjustable connector includes two relatively re-orientatable members, each having a lockable universal joint and a connecting member for connecting the two relatively re-orientatable members, whereby when the two relatively re-orientatable members are connected the two joints are in mechanical communication via the connecting member, and
wherein at least one of the universal joints enables linear movement between the two relatively re-orientatable members.

* * * * *